US010119983B2

(12) United States Patent
Hoffmann et al.

(10) Patent No.: US 10,119,983 B2
(45) Date of Patent: Nov. 6, 2018

(54) SAMPLE MANIPULATION DEVICE (71) Applicant: Hamilton Bonaduz AG, Bonaduz (CH)

(72) Inventors: Peter Hoffmann, Bergen auf Ruegen (DE); Martin Frey, Reichenburg (CH); Beat Zahner, Kaltbrunn (CH); Petra Tappe, Chur (CH)

(73) Assignee: HAMILTON BONADUZ AG, Bonaduz (CH)

( * ) Notice: Subject to any disclaimer, the term of this patent is extended or adjusted under 35 U.S.C. 154(b) by 145 days.

(21) Appl. No.: 15/104,152

(22) PCT Filed: Dec. 5, 2014

(86) PCT No.: PCT/EP2014/076673
§ 371 (c)(1),
(2) Date: Jun. 13, 2016

(87) PCT Pub. No.: WO2015/086445
PCT Pub. Date: Jun. 18, 2015

(65) Prior Publication Data
US 2016/0320423 A1    Nov. 3, 2016

(30) Foreign Application Priority Data
Dec. 13, 2013    (DE) .......................... 10 2013 114 041

(51) Int. Cl.
*G01N 35/04*    (2006.01)
*G01N 35/02*    (2006.01)
(Continued)

(52) U.S. Cl.
CPC .......... *G01N 35/04* (2013.01); *B01L 3/50825* (2013.01); *G01N 35/00732* (2013.01);
(Continued)

(58) Field of Classification Search
None
See application file for complete search history.

(56) References Cited

U.S. PATENT DOCUMENTS

2006/0210446 A1*  9/2006  Higuchi .............. G01N 35/028
                                                                422/510
2008/0190735 A1*  8/2008  Luoma ..................... B01L 9/00
                                                                198/340
(Continued)

FOREIGN PATENT DOCUMENTS

EP           1640723 A1       3/2006
JP        2009229109 A       10/2009
(Continued)

OTHER PUBLICATIONS

SBS Guidelines, *American National Standards Institute, Society for Biomolecular Sciences*, ANSI/SBS Jan. 2004, ANSI/SBS Feb. 2004, ANSI/SBS Mar. 2004, ANSI/SBS Apr. 2004, Jan. 25, 2006-Jan. 27, 2006, 40 pages.

*Primary Examiner* — Benjamin R Whatley
(74) *Attorney, Agent, or Firm* — Seed IP Law Group LLP (57) ABSTRACT

Described herein are sample manipulation devices, for removing lids from and/or for placing lids onto sample containers. Such devices include a sample unit including a sample carrier receptacle for receiving at least one sample carrier for holding one or more sample containers, and a manipulation unit having at least one manipulation tool, where the sample unit and the manipulation unit are movable relative to each other along a movement direction. The sample unit is also movable between a first orientation in which a longitudinal direction of a sample carrier in the sample carrier receptacle is parallel to the movement direction between sample unit and manipulation unit, and a second orientation in which a transverse direction, which is orthogonal to the longitudinal direction, of a sample carrier (Continued)

in the sample carrier receptacle is parallel to the movement direction between sample unit and manipulation unit.

18 Claims, 8 Drawing Sheets

(51) Int. Cl.
  G01N 35/00 (2006.01)
  B01L 3/00 (2006.01)
  B01L 9/00 (2006.01)

(52) U.S. Cl.
  CPC ............ *G01N 35/028* (2013.01); *B01L 9/523* (2013.01); *G01N 2035/00801* (2013.01); *G01N 2035/0405* (2013.01)

(56) References Cited

U.S. PATENT DOCUMENTS

| | | | |
|---|---|---|---|
| 2011/0200419 A1* | 8/2011 | Yamasaki | G01N 35/028 414/796.9 |
| 2013/0116102 A1* | 5/2013 | Hansen | B04B 11/043 494/10 |
| 2014/0193300 A1* | 7/2014 | Bernhard | G01N 35/04 422/64 |

FOREIGN PATENT DOCUMENTS

| | | | | |
|---|---|---|---|---|
| WO | 2012059701 A2 | 5/2012 | | |
| WO | WO-2012059701 A2 * | 5/2012 | ............. | B01L 9/523 |

* cited by examiner

SAMPLE MANIPULATION DEVICE

BACKGROUND

Technical Field

The present invention relates to a sample manipulation device comprising a sample unit for receiving at least one sample container, as well as a manipulation unit having at least one manipulation tool. The sample unit and the manipulation unit are movable relative to each other along at least one movement direction.

Description of the Related Art

The sample manipulation device described here is to be designed for removing lids from sample containers and/or placing lids onto sample containers. The sample containers contain in particular samples having at least one phase present in a flowable state, i.e., in liquid or viscous form. For example, the sample to be treated may contain microbiological or other material, as it is treated in biochemical, pharmaceutical, genetic or medical industry and research, respectively. An as efficient as possible and automated course of sample treatment is desirable in this respect, especially in applications in which a large quantity of samples is to be treated.

The samples to be treated are contained in sample containers which as a rule can be closed by means of a lid so as to seal the sample contained in the sample container with respect to the environment. This is of relevance e.g., in case of microbiological samples, when the samples following a treatment are to be kept hermetically sealed for a certain incubation time. The lids can be removed again when the sample is to be treated further upon expiration of the incubation time. The manipulation device of the type described here is to serve in particular for closing the sample containers by means of a lid and for removing the lid, respectively. The term lid is to be understood here quite generally, in the sense of any construction for closing the sample container, for example in the form of plugs, stoppers or the like. In many situations, the lid will have the configuration of a screw cap.

In general, a plurality of sample containers will be accommodated in a sample carrier and be treated in parallel. For the sample carrier, certain standardized formats have become established, according to which a specific number of sample containers can be arranged in matrix-like manner in respective sample receptacles. Frequently, there are formats used for the sample carriers as these are standardized according to the SBS Guidelines (Society of Biomolecular Sciences, e.g., in accordance with ANSI/SBS 1-2004, ANSI/SBS 2-2004, ANSI/SBS 3-2004, ANSI/SBS 4-2004). Such a sample carrier may comprise, for example, 48 sample receptacles in an arrangement of 6 lines with 8 sample receptacles each, 96 sample receptacles in an arrangement of 8 lines with 12 sample receptacles each, 394 sample receptacles in an arrangement of 16 lines with 24 sample receptacles each, or 1536 sample receptacles in an arrangement of 32 lines with 48 sample receptacles each.

The document JP 2009 229109 A discloses a sample manipulation device in which sample containers can be automatically opened and closed again.

The format of the sample carriers for samples to be treated in succession often changes in the course of a process. Even if only sample carriers of one and the same configuration are to be used at all times (e.g., sample carriers with 96 sample receptacles), there is often the problem that individual sample carriers to be treated in succession in a process should be treated in different orientations. This is why relatively troublesome readjustment processes are necessary as a rule so far in the sample manipulation device, before samples can be treated that are received in a sample carrier with a different format—which is to be understood as sample carriers of different configuration in the same or a different orientation as well as sample carriers with different orientations, but otherwise the same configuration.

BRIEF SUMMARY

Embodiments are directed to a sample manipulation device of the type described hereinbefore, which is compatible with sample carriers of different formats without complex readjustment process.

The present invention suggests a sample manipulation device, in particular for removing lids from sample containers and/or for placing lids onto sample containers, comprising a sample unit and a manipulation unit having at least one manipulation tool. The sample unit and the manipulation unit are movable relative to each other along a movement direction. The sample unit has at least one sample carrier receptacle for receiving at least one sample carrier which extends in a longitudinal direction and a transverse direction orthogonal to said longitudinal direction and serves to hold one or more sample containers. Furthermore, the sample unit is transferable between a first orientation in which the longitudinal direction of a sample carrier received in the sample carrier receptacle is parallel to the movement direction between sample unit and manipulation unit, and a second orientation in which the transverse direction of a sample carrier received in the sample carrier receptacle is parallel to the movement direction between sample unit and manipulation unit.

The sample unit and/or the manipulation unit is to be movable in particular in the sense of a movement direction between an advancing direction and/or a retreating direction opposite to the advancing direction, so that it is possible to displace the sample unit relative to the manipulation unit between a manipulation position—in which the manipulation tool processes the sample contained in the sample carrier—and a rest position or optionally a storage position—in which the manipulation tool is located in movement direction in a predetermined distance from the sample received in the sample carrier. The sample unit and/or the manipulation unit in particular is to be supported so as to be linearly movable in the movement direction.

When reference is made to a sample carrier in the following, there is regularly meant a sample carrier inserted in the sample carrier receptacle, unless described otherwise. The sample carrier receptacle as a rule is designed such that the sample carrier can be inserted into the sample carrier receptacle in one orientation only or at the most in a countable multiplicity of selected orientations.

The term relating to the transferability of the sample unit between first and second orientations is to express primarily that the sample unit is designed such that a sample carrier received in the sample carrier receptacle can be transferred between first and second orientations. I.e., the sample carrier inserted in the sample carrier receptacle is to be transferable from the first orientation to the second orientation, and vice versa. This can be effected easiest by designing the sample carrier receptacle such that the sample carrier can be inserted in the sample carrier receptacle selectively either in the first orientation or in the second orientation. By removing a sample carrier inserted in the sample carrier receptacle in the first orientation and by inserting the same sample carrier or a different sample carrier having the same or an at least compatible configuration into the sample carrier receptacle in the second orientation, it is then possible to achieve the afore-mentioned transferability between first and second orientations. A corresponding configuration will still be described in more detail in the following with reference to an optional sample lid carrier receptacle. For avoiding the repetitions, reference is made to these statements which are applicable analogously here as well.

However, it is by far more expedient to design the sample unit such that the sample carrier, for transfer from the first to the second orientation or vice versa, need not be removed from the sample carrier receptacle. As a rule, the sample carrier receptacle itself then will be designed so as to be movable.

Even if the position of the sample carrier with respect to the manipulation tool changes when the sample unit is transferred between first and second orientations, such a transfer of the sample unit in general does not yet entail a displacement of the sample unit with respect to the manipulation unit in the movement direction. Rather, the displaceability of the sample unit in the movement direction and the transferability of the sample unit between first and second orientations in this sense are in many cases independent of each other.

In particular, the sample unit furthermore is to be transferable between first and second orientations in a plane defined by the longitudinal direction and the transverse direction of a sample carrier received in the sample carrier receptacle in the correct position. In this context, the transfer direction between first and second orientations is to be parallel to this plane. Moreover, a sample carrier received in the sample carrier receptacle in positionally correct manner, in the operating position, will be arranged substantially horizontally. This holds, for example, for a device for manipulating liquid samples.

The transferability of the sample unit between first and second orientations permits a quite simple and rapidly implementable possibility of inserting and treating sample carriers of different formats in the sample carrier receptacle in succession. The sample carriers can be inserted into the sample carrier receptacle always in the same manner, and the sample unit may be transferred to the first or second orientation only thereafter, if desired. The variant that the sample carrier receptacle itself is displaceable between first and second orientations is particularly preferred for this reason. To this end, there may also be made provisions that the sample unit can be transferred into a third orientation in which the sample carrier is inserted into the sample carrier receptacle. From the third orientation, the sample unit then is transferred either to the first or the second orientation, as desired.

Both the insertion of the sample carrier and the transfer of the same to the first and/or second orientation can be effected in largely automated manner, so that also the successive treatment of samples received in different sample carriers can be automated without any problem and can be handled without significant time delay.

As regards the formats that can be handled, reference may be made to the formats mentioned hereinbefore in accordance with the SBS standard. It is to be pointed out furthermore that it is not only possible to process different sample carriers, but also sample containers in a large variety of different configurations.

In many situations, the dimension of the sample carrier will be larger in longitudinal direction than in transverse direction. This situation is present, for example, in case of the aforementioned sample carriers according to the SBS Guidelines (with 48 sample receptacles in 6 lines with 8 sample receptacles each; 96 sample receptacles in 8 lines with 12 sample receptacles each; 394 sample receptacles in 16 lines with 24 sample receptacles each; 1536 sample receptacles in 32 lines with 48 sample receptacles each; and so on). For receiving the sample carriers in the correct position, the associated sample carrier receptacle as a rule will thus be larger—at least roughly—in longitudinal direction than in transverse direction. Depending on how the larger one of the two dimensions of the sample carriers—which in the following will be referred to as longitudinal direction—is arranged in relation to the movement direction, it is possible—following common paper formats—to speak of a "landscape" arrangement when the sample carriers are to be processed with their longitudinal direction being arranged orthogonal to the movement direction and, respectively, to speak of a "portrait" arrangement when the sample carriers are to be processed with their longitudinal direction being arranged parallel to the movement direction. The transferability of the sample unit between first and second orientations according to the invention permits furthermore to insert and/or process successive sample carriers in the sample carrier receptacle in arbitrary manner in a landscape or a portrait arrangement.

Quite a number of common sample carriers have a first axis of symmetry extending in the longitudinal direction and a second axis of symmetry, orthogonal to the first axis of symmetry, extending in the transverse direction. The sample carrier receptacle provided for receiving such sample carriers then as a rule will have a corresponding axis of symmetry as well. For example, this is the case for substantially rectangular sample carriers, like the aforementioned SBS sample carriers, and the sample carrier receptacle provided for receiving such sample carriers will be substantially rectangular and complementary to the sample carrier as well. The term "substantially" in this context is to point out that there may be indeed certain deviations from the basic shape, for example in the form of a chamfered corner or projections, in order to make sure that a sample carrier—with regard to the first or second orientation each—can be inserted into the associated sample carrier receptacle only in one single "positionally correct" orientation.

For effecting the transfer between first orientation and second orientation, it is expedient to design the sample carrier receptacle so as to be rotatable about an axis of rotation that is orthogonal to the plane defined by the longitudinal direction and the transverse direction, in particular about a vertical axis of rotation. When the sample carrier receptacle is rotated, a sample carrier inserted in the sample carrier receptacle will rotate concomitantly therewith, but at all times is kept within the plane defined by the sample carrier. If, in addition thereto, the axis of rotation—with respect to a sample carrier received in the sample carrier receptacle—is arranged centrally, a particularly space-saving setup of the sample unit is achieved. Furthermore, the position of the sample carrier receptacle remains the same with respect to the movement direction in the first orientation and the second orientation. For example, in case of a rectangular sample carrier receptacle for receiving rectangular sample carriers, the respective axes of symmetry pointing in the movement direction are located exactly on top of each other in both orientations. The manipulation tool thus can perform the same movement pattern in both orientations of the sample unit. Arranged centrally in this context is to be understood such that the axis of rotation is arranged within the outline of the sample carrier inserted in the sample carrier receptacle, with the distance to the edges of the sample carrier being as equal as possible. In an embodiment, the axis of rotation may extend e.g., in the vertical direction and thus may intersect both the first and the second axis of symmetry.

For transferring the sample unit between first and second orientations, the sample manipulation device may comprise furthermore a rotary drive acting on a sample carrier received in the sample carrier receptacle, for rotating the same at least between the first and second orientations. To this end, an electric servo drive is especially expedient. In many cases, the sample carrier receptacle can be coupled in non-rotatable manner with a sample table that is rotatable about a vertical axis. The rotary drive can then expediently act on such a sample table. Besides, the sample table may also have the sample carrier receptacle formed therein such that the rotary drive acts directly onto the component having the sample carrier receptacle formed therein.

For example, the construction may be such that the sample table has at least one circular peripheral surface formed thereon for cooperation with the rotary drive. Depending on the diameter of this peripheral surface, a desired step-down ratio can be realized so that a servo drive with high nominal speed, but correspondingly low nominal torque can be used. This permits the realization of a compact and inexpensive drive, allowing an adjustment of the sample unit between first orientation and second orientation, and optionally also further orientations, if desired, to be realized in inexpensive manner—and moreover in automated manner, if desired.

For example, the rotary drive may be in the form of a direct drive. In an embodiment as a positive direct drive, the circular peripheral surface of the sample table may have teeth cooperating with an output pinion of the rotary drive. In an alternative, frictional variant, the circular peripheral surface may also have a driving surface which frictionally cooperates with an output wheel of the rotary drive. Apart from the variant as direct drive, there are also other variants conceivable, e.g., such that the rotary drive acts on a circular peripheral surface of the sample table by way of a toothed belt or driving belt.

In further embodiments, optionally in addition to the feature combinations already mentioned, the sample carrier receptacle may be rotatably supported in a sample carriage that is displaceable in the movement direction. The movement of the sample unit relative to the manipulation tool—e.g., for arranging the manipulation tool above a respective sample received in the sample carrier, or for processing a sample by means of the manipulation tool—can thus be separated quite easily from the movement of the sample carrier receptacle for transferring the sample unit between first and second orientations. Sample table and sample carriage may indeed be of integral design, provided that measures are taken that the rotary drive for transferring the sample unit between first and second orientations engages the sample table in such a manner that the latter does not move also in the movement direction at the same time. Optionally, corresponding braking or blocking means will have to be provided then. Frequently, it will be constructionally more expedient to form the sample table and the sample carriage as separate components. For, the sample table then may be supported in/on the sample carriage in rotatable manner, so that the rotary drive acting on the sample table as a rule will not have effects on the relative position of the sample carriage with respect to the manipulation tool. For moving the sample carriage in the movement direction in addition, there may be provided e.g., a linear drive on the sample carriage for movement in an advancing direction and/or in a retreating direction opposite to the advancing direction.

Furthermore, it is advantageous when the sample carriage—in addition to the sample carrier receptacle—comprises a sample lid carrier receptacle in which a sample lid carrier associated with the respective sample carrier can be received. Lids removed from the samples held in the sample carrier may then be easily deposited in the associated sample lid carrier—either temporarily or, if desired, also permanently. In this respect, it is particularly advantageous when the sample lid carrier has a configuration corresponding substantially to the sample carrier, in particular with respect to the arrangement of the individual sample receptacles and sample lid receptacles, respectively. When the sample carrier receptacle is transferable between first and second orientations, it is expedient furthermore when also the sample lid carrier receptacle is designed such that, both in the first orientation of the sample carrier receptacle and in the second orientation of the sample carrier receptacle, the respectively associated sample lid carrier is arranged in the correct position with respect to the respective sample carrier received in the sample carrier receptacle. For example, when the sample carrier receptacle is oriented in a portrait arrangement, the associated sample lid carrier receptacle should be oriented in a portrait arrangement as well. The same applies correspondingly for a sample carrier receptacle arranged in a landscape arrangement. To this end, it is possible e.g., to provide a sample lid carrier receptacle which—in a plan view—has an outline resulting from a combination of the outlines of two sample carrier receptacles rotated relative to each other by an angle of 90 degrees about the common axis of rotation of the same. The sample lid carrier receptacle then has a substantially cross-shaped outline in a plan view.

The sample lid carrier receptacle can be formed with a stationary sample lid carrier. The latter then preferably should be formed such that it combines the configuration of a sample lid carrier arranged in the first orientation and a sample lid carrier arranged in the second orientation. However, more flexibility is obtained when only the sample lid carrier receptacle in the sample carriage is of stationary design and the respective appropriate sample lid carriers are inserted in the sample lid carrier receptacle. According to a further possibility, the sample lid carrier may combine the configuration of a sample lid carrier arranged in a first orientation and a sample lid carrier arranged in a second orientation.

For displacing the sample unit in relation to a fixed manipulation unit, the sample manipulation device, furthermore, can comprise a linear drive acting on the sample unit. This linear drive can be formed, for example, by an electric servo drive with corresponding linear guiding elements and/or linear driving elements, such as e.g., a threaded spindle. The linear drive can be arranged in space-saving manner underneath the sample unit. In particular, the linear drive can engage with the sample carriage laterally and/or from below. This is particularly suitable in situations in which the manipulation tool approaches the sample carriage from above—which is the most common practice for removing and attaching lids, respectively.

The manipulation tool can be mounted to the manipulation unit so as to be rotatable about a vertical axis and movable in the vertical direction, so that the manipulation tool can be moved towards the sample unit from above. For example, the manipulation tool may be suspended on the manipulation unit, i.e., it can be mounted to a supporting structure so as to extend from above downwardly, with the supporting structure itself being movable in at least one direction, for example in vertical direction.

For simultaneously processing a plurality of sample containers arranged in a series or row, the manipulation unit may have a plurality of manipulation tools that are lined up in a direction orthogonal to the vertical plane defined by the movement direction.

In a particular advantageous configuration, the sample manipulation device may comprise a manipulation unit having a tool head that is exchangeably mounted on a tool carrier, with the tool head—in the coupled position—being movable in its entirety in vertical direction and the at least one manipulation tool being mounted on the tool head so as to be rotatable about a vertical axis. This configuration permits rapid and flexible matching of the manipulation unit for processing a large variety of different sample carriers and even different sample containers, by simply exchanging the tool head present in its entirety. The configuration described here with exchangeable tool head appears to be so advantageous that the applicant perceives therein a subject matter justifying protection of its own in comparison with the features of claim 1 and thus reserves himself the right to direct a separate, independent claim thereto, which in particular is independent of the feature whether the sample unit is transferable between first and second orientations.

In a further preferred development, the sample manipulation device may comprise furthermore a sample container identification device for identifying the sample carrier and/or individual sample containers located in the sample carrier—which is inserted in the sample carrier receptacle. The sample container identification device in space-saving manner may be formed such that it is capable of recognizing identification patterns located at the bottom of a respective sample container. This can be effected e.g., by an optical sensor.

BRIEF DESCRIPTION OF THE SEVERAL VIEWS OF THE DRAWINGS

The invention will now be explained in more detail with reference to embodiments shown in the drawings, in which.

DETAILED DESCRIPTION

Figure 1:
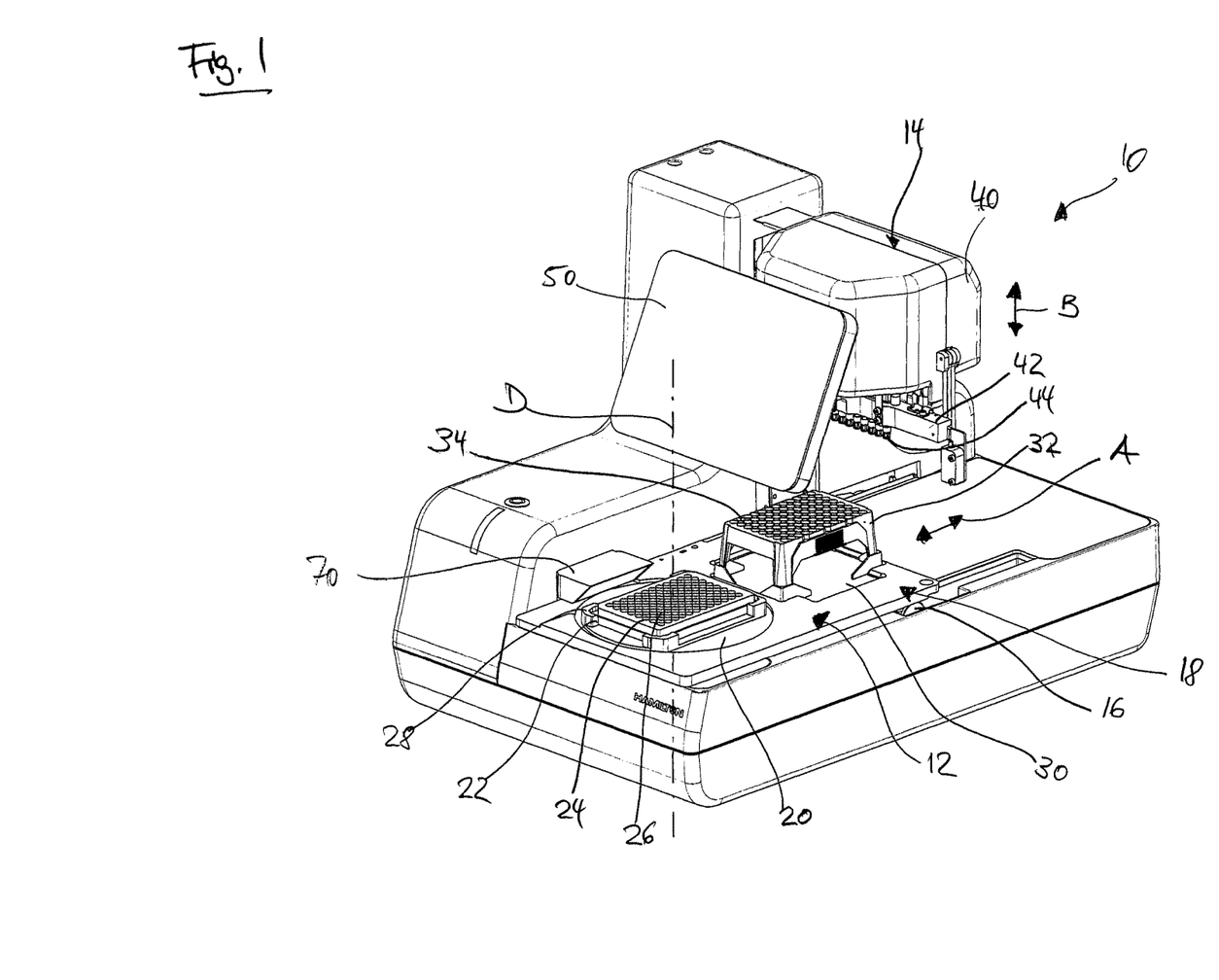
FIG. 1 shows a perspective view of an embodiment of a sample manipulation device according to the invention, with sample carrier and sample lid carrier being arranged in a portrait orientation.

The perspective view of an exemplary embodiment of a sample manipulation device 10 according to the invention, as illustrated in FIG. 1, comprises a sample unit generally designated 12 and a manipulation unit generally designated 14. Sample unit 12 and manipulation unit 14 are linearly displaceable relatively to each other in a movement direction illustrated by double arrow A. In the embodiment illustrated in FIG. 1, the movement direction extends in a horizontal plane. The relative displacement described between sample unit 12 and manipulation unit 14 in the movement direction, in the embodiment illustrated in FIG. 1, is effected in that the sample unit 12 is movable by means of a linear drive, of which FIG. 1 shows an output driving wheel 16 underneath the sample unit 12, in relation to the manipulation unit 14—which in any case is not movable in the movement direction A—in an advancing or feeding direction (in FIG. 1 obliquely towards the rear) or in a retreating direction (in FIG. 1 obliquely towards the front). The output driving wheel 16 of the linear drive acts on the bottom side of a sample carriage 18 of sample unit 12. The sample carriage 18 itself is movably guided in movement direction A on a linear guiding assembly formed in the housing of the sample manipulation unit 10.

In addition to sample carriage 18, the sample unit 12 comprises a rotary table 20 which is rotatably supported about an axis of rotation orthogonal to the rotary table. The axis of rotation is illustrated in FIG. 1 in broken lines and designated D. In case of the horizontal orientation of the sample table 18, as illustrated in FIG. 1, the axis of rotation D extends in vertical direction.

The rotary table 20 has a sample carrier receptacle 22 formed therein into which a sample carrier, illustrated at 24 in FIG. 1, can be inserted. The sample carrier 24 in FIG. 1 has a substantially rectangular shape with a longer longitudinal side and a shorter transverse side. The sample carrier 24 has a plurality of individual sample receptacles formed therein in matrix-like manner, one thereof being illustrated in FIG. 1 in exemplary manner at 26. The sample receptacles 26 are arranged in rows and columns in which in accordance with the language usage applied here, in an operative position of the sample carrier 24, a row at all times is to extend transverse to the movement direction A and a column at all times is to extend in the movement direction. The sample carrier 24 is associated with a respective sample carrier receptacle 24 in the sense that the respective sample carrier 24 fits into the respective sample receptacle 24 in only one orientation, or in at the most some few mutually rotated orientations (for example, two orientations rotated relative to each other by 90 degrees, two orientations rotated relative to each other by 180 degrees, four orientations rotated relative to each other by 90 degrees each). Thus, the outlines of sample carrier 22 and respectively associated sample carrier receptacle 24 are largely in correspondence with each other. In the variant shown in FIG. 1, such a corresponding design is realized in a manner that the sample carrier receptacle, at the four corner portions, has a respective frame member 28 of increased height, so that the four frame members together define the outline of a rectangle, the dimensions of which correspond to the also rectangular outline of the sample carriers 22.

The sample manipulation device 10 illustrated in FIG. 1 is provided with a sample carrier receptacle 22 for receiving sample carriers 24 in accordance with the SBS standard described hereinbefore, with express reference being made here to the description thereof. In the variant shown in FIG. 1, the sample carrier receptacle 22 is designed for substantially rectangular SPS sample carriers 24 in a configuration with 12 rows and 8 columns, i.e., a total of 96 sample receptacles. Other sample carrier configurations and sample container configurations, respectively, can be processed easily by exchanging the rotary table 20. When the numerical dimensions are compatible in longitudinal and transverse directions, different configurations can be processed in still easier manner, by exchanging only the respective sample carrier receptacle 22 and without exchanging the rotary table 20.

The sample unit 12 comprises furthermore a sample carrier lid receptacle 13 in which a sample lid carrier designated 32 in FIG. 1 can be inserted. The sample lid carrier 32 has a plurality of sample lid receptacles formed therein, one thereof being designated 34 in FIG. 1 in exemplary manner. The sample lid carrier 32 has a configuration which—in particular with regard to the matrix-like arrangement of the sample lid receptacles 34 in rows and columns—corresponds to the configuration of the sample carrier 24 inserted in the sample carrier receptacle 22. The individual sample lid receptacles 34 of the sample lid carrier 32 are designed to receive a lid of a sample container located in the respectively associated sample receptacle 26 of sample carrier 24.

In particular, both the sample carrier 24 and the sample lid carrier 32 in FIG. 1 are oriented in a portrait arrangement, i.e., such that the longitudinal sides of the same extend in the movement direction A. The same holds correspondingly for an alternative arrangement, in which both the sample carrier 24 and the sample lid carrier 32 are oriented in a portrait arrangement, i.e., such that the longitudinal sides of the same extend transverse to the movement direction A (cf. for example FIG. 2). This considerably facilitates many processes, for example the placement of lids onto sample containers and the removal of lids from sample containers, respectively, the transport of lids from the sample carrier 24 to the sample lid carrier 32 and vice versa, respectively, or the placement of lids in the sample lid carrier 34 and the taking up of lids from the sample lid carrier 34, and in particular permits a process in which the contamination of already opened samples can be effectively avoided. The sample lid carrier receptacle 32 has a substantially cross-shaped outline—as seen from above—which results from a combination of two sample lid carrier receptacles rotated about their center by an angle of 90° relative to each other, which are each associated with a sample carrier 24 in portrait arrangement and a sample carrier 24 in landscape arrangement. A sample lid carrier 34 thus can be inserted in the sample lid carrier receptacle 32 in four orientations rotated relative to each other by 90 degrees each.

The manipulation unit 14 comprises a tool head 40 having a tool carrier 42. The tool carrier 42 has the configuration of a bar arranged transverse, in particular orthogonal, to the movement direction A. The tool carrier 42 has a plurality of manipulation tools mounted thereon side by side, of which one is designated 44 in FIG. 1 in exemplary manner. The manipulation tools 44 are each supported so as to be rotatable about an axis orthogonal to the tool carrier 42. The manipulation tools 44 are each driven for rotation about their axis by a servo drive accommodated in the tool head 40. The individual manipulation tools 44 each serve for removing and placing lids from and onto sample containers, respectively. In the variant illustrated in FIG. 1, this is effected by threadedly engaging and threadedly disengaging the lids, respectively, upon guiding of the respective tool 24 to the associated lid.

The sample manipulation unit 10 shown in FIG. 1 comprises furthermore a touch-sensitive screen 50 via which control commands can be entered, and which displays status information as well as additional relevant information during operation, respectively. In the lower portion, approx. at the height of the sample containers inserted in the sample carrier receptacle 24, there is provided furthermore a sample identification device 70 which is arranged such that it is capable of recognizing identification patterns applied to the sample containers. This facilitates the automated passage of samples in large numbers. In particular, the sample identification device 70 is arranged such that it is capable of detecting identification patterns located at the bottom of individual sample containers. This detection can take place in particular with the aid of a suitably mounted optical sensor.

Figure 2:
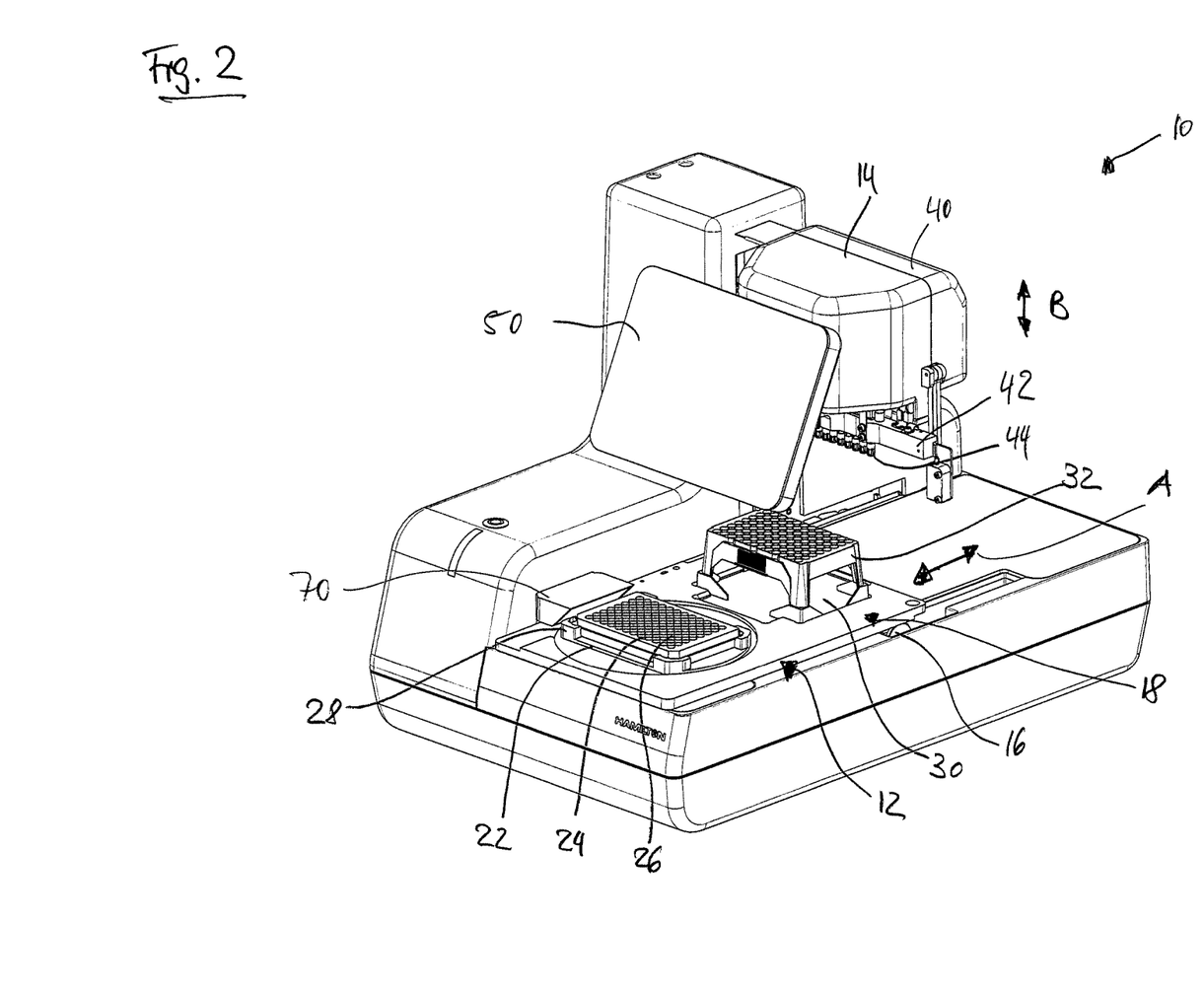
FIG. 2 shows a perspective view of the same sample manipulation device according to the invention, with sample carrier and sample lid carrier being arranged in a landscape orientation.

FIG. 2 shows, in a perspective view corresponding to FIG. 1, an embodiment of the same sample manipulation device 10 with sample carrier 24 and sample lid carrier 32 in a landscape orientation, in which the long sides both of the sample carrier 24 and of the sample lid carrier 32 extend orthogonal to the movement direction A. In the landscape orientation, the rows thus contain a larger number of sample containers than the columns. This permits a higher throughput in case the manipulation unit 14 has a correspondingly large number of manipulation tools 44. The reference numerals used in FIG. 2 correspond to those used in FIG. 1. For avoiding repetitions, reference is made to the description relating to FIG. 1.

According to the invention, the sample unit 12 is transferable between a first orientation, namely the portrait orientation illustrated in FIG. 1, and a second orientation, namely the landscape orientation illustrated in FIG. 2. The transfer between first and second orientations takes place preferably such that the sample carrier receptacle 22 is displaceable between the first orientation illustrated in FIG. 1 and the second orientation illustrated in FIG. 2. This displacement basically can be effected manually. However, it is more convenient when, as in case of FIGS. 1 to 6, the transfer between first orientation and second orientation is effected with the aid of a drive. To this end, there may be provided an electric servo drive which will be described in some more detail in the following.

Figure 3:
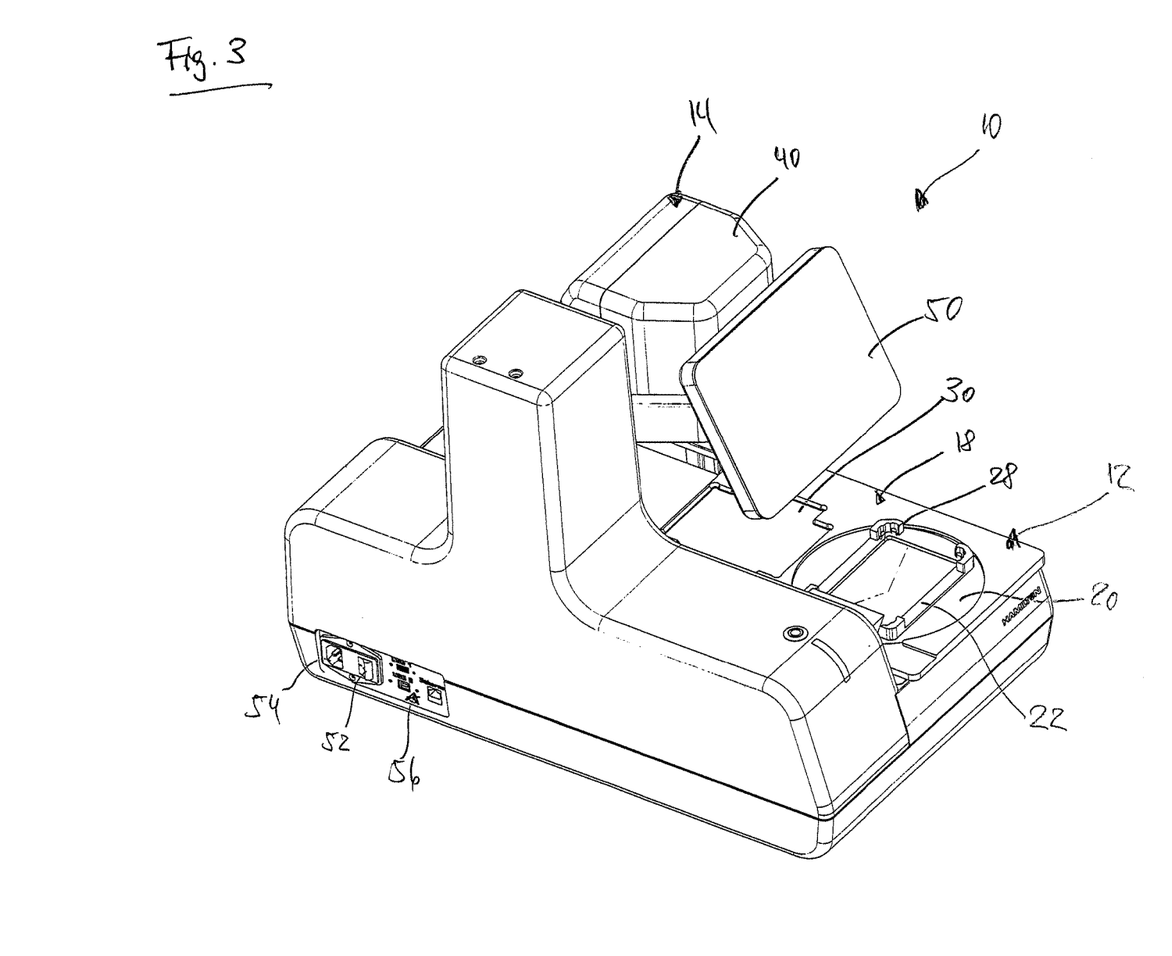
FIG. 3 shows another view, from a different perspective and without sample carrier and sample lid carrier, illustrating a sample carrier receptacle in a landscape orientation and a cross-shaped sample lid carrier receptacle.

In the illustration of the sample manipulation device 10 shown in FIG. 3, which is a perspective from the rear of FIG. 1 and FIG. 2, respectively, neither sample carriers nor sample lid carriers are inserted in their respective receptacle. The sample carrier receptacle 22 is arranged in landscape orientation. The illustration clearly shows the cross-shaped outline of the sample lid carrier receptacle 30, which comprises an outline design that is compatible both with the sample carrier receptacle 22 in landscape orientation and with the sample carrier receptacle 22 in portrait orientation.

In addition to the components already described with regard to other figures, to the further description of which express reference is being made here, the illustration according to FIG. 3 shows in addition a supply port 54 for connection to an electricity supply network, as well as an on/off switch 52 and a number of ports, generally designated 56, for connection to an internal or external computer network, either by wire or in wireless manner.

Figure 4A:
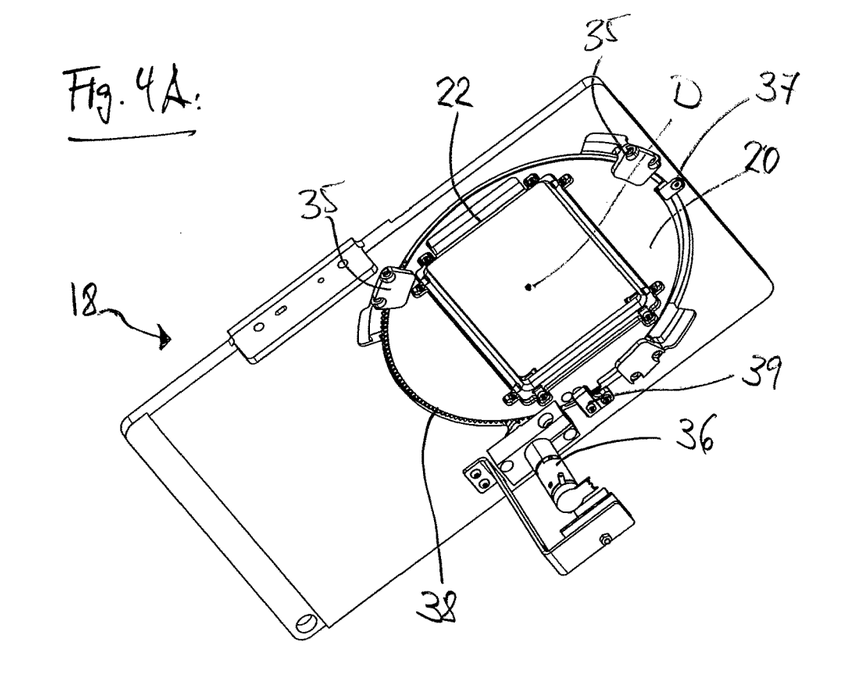
FIG. 4A shows a perspective bottom view of a sample carriage along with a sample table having a rotary drive for transferring the sample carrier receptacle between first and second orientations.

FIG. 4A shows, in a perspective view from below, a sample carriage 18 along with rotary table 20, in which the sample carrier receptacle 22 is formed. On the bottom side of the rotary table 20, there is mounted a rotary drive 36—in the present embodiment in the form of an electric servo drive. The output pinion of the rotary drive 36 meshes with teeth 38 provided on a circular peripheral surface of the rotary table 20 in a sector range of at least 90°. Thus, the rotary drive 36 directly drives the rotary table 20 via the teeth 38, so as to transfer the sample carrier receptacle 22 from the first orientation (portrait orientation) thereof to the second orientation (landscape orientation) thereof, or vice versa. As rotary drive 36, there can be used a fast-rotation and thus compact—with regard to a given nominal power—electric servo drive (e.g., a DC motor or a brushless DC motor), the high speed of which is converted into slower rotation of the rotary table 20 about the axis of rotation D illustrated in FIG. 3, via the engagement between output wheel of the rotary drive 36 and the teeth 38 having the effect of a reduction gear system. Due to the reduction, there is created a sufficiently large torque for rotating the rotary table 20, possibly inclusive of sample carrier 24 and all sample containers received in the sample carrier 24, and for being able to stop the assembly, once the first or second orientation has been reached. The exact starting and keeping the first and second orientations, respectively, is monitored with the aid of at least one rotation sensor 39 which also is mounted on the bottom side of the sample carriage 20 along the periphery of rotary table 20 and facing the same. For rotatably supporting the rotary table 20 in the sample carriage 18, there are mounted several bearings 35 along the periphery of rotary table 20. Besides, a stop 37 provided at the periphery of rotary table 20 as well makes sure that the rotary table is inserted in the sample carriage 20 in an orientation such that the teeth 38 on the periphery of the rotary table 20 cooperate or mesh with the output pinion of the rotary drive 36.

Figure 4B:
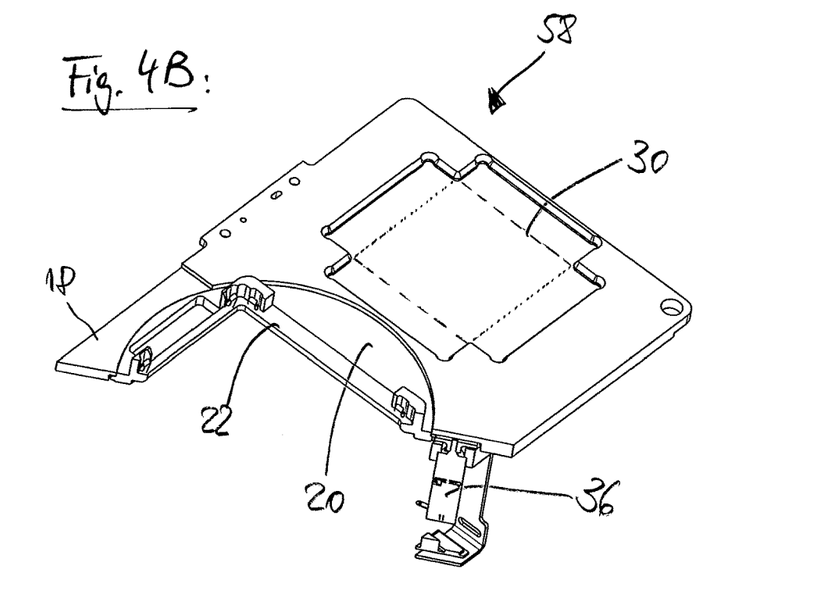
FIG. 4B shows a perspective top view of a top attachment for the sample table of FIG. 4A, having a sample lid carrier receptacle formed therein.

FIG. 4B shows, in a perspective view from above, a top attachment 58 on sample carriage 18 of FIG. 4A along with a sample lid carrier receptacle 30 formed therein. Also illustrated is a section of sample carriage 18 and of rotary table 20 which is rotatable with respect to the same and has the sample carrier receptacle 22 formed therein. Clearly visible is the, in a plan view, substantially cross-shaped outline of the sample lid carrier receptacle 30, which results when the outline of a sample lid carrier receptacle arranged in landscape orientation (cf. the broken lines in FIG. 4B) is combined with the outline of a sample lid carrier receptacle arranged in portrait orientation (cf. the dotted lines in FIG. 4B). The cross-shaped outline of the sample lid carrier receptacle 30 permits insertion of sample lid carriers 34 in four orientations relatively rotated by 90 degrees each.

Figure 4C:
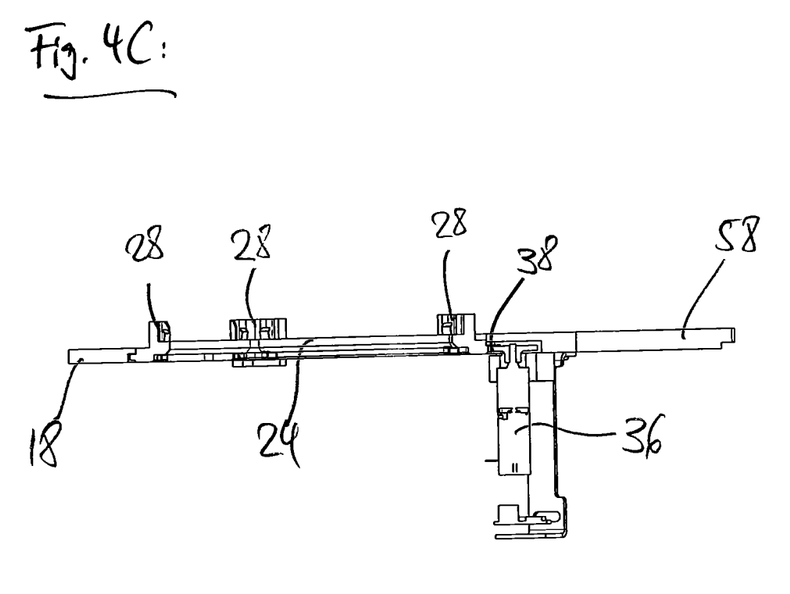
FIG. 4C shows a side view of the sample carriage of FIG. 4A along with the top attachment of FIG. 4B.

The side view illustrated in FIG. 4C shows the sample carriage 18 of FIG. 4A along with the top attachment 58 of FIG. 4B.

Figure 5:
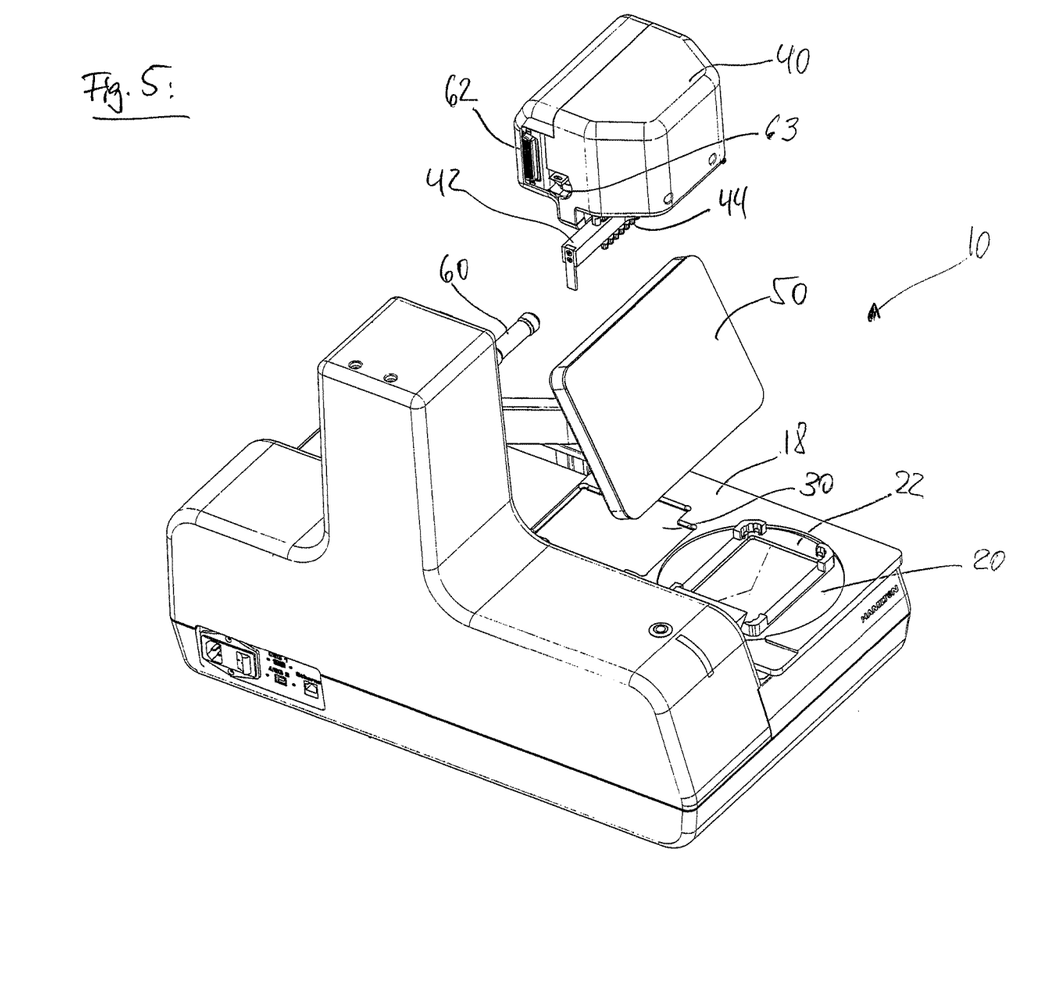
FIG. 5 shows an illustration of the sample manipulation device of FIG. 3 with the tool head being removed.

FIG. 5 shows the sample manipulation device 10 of FIG. 3 with removed tool head 40. It can be seen that the tool head 40 along with the tool carrier 42 and the manipulation tools 44 suspended thereon can be removed as a unit from the housing of the sample manipulation device 10. Attachment of the tool head 42 to the housing is effected by means of a stub axle 60 that is adapted to be releasably coupled to the tool head 40. In the coupled position, the stub axle is inserted into a recess 63 formed on tool head 40 (cf. also FIG. 6). The stub axle 60 itself is driven in vertical direction by a drive of its own that is accommodated in housing 60, so that the tool head 40 attached thereto can be moved upwardly and downwardly, respectively, in its entirety, i.e., along with all tools suspended on tool carrier 42. FIG. 5 also illustrates a side of an electric plug connection 62 which is provided on tool head 40 and, when the tool head 40 is mounted on stub axle 60, is coupled with a mating counter-connection on the housing and thus establishes an electric connection between tool head 40 and housing. By way of this connection, control commands and data for controlling the drive of the individual tools 44 are exchanged on the one hand, and sensor data concerning the position and the state of the tool head 40 are sent back to a central control unit provided in the housing, on the other hand. If desired, the rotary drive for the individual tools 44 may be accommodated in the housing as well. In that event, the coupling between tool head 42 and stub axle 60 is selected such that a rotational drive for the individual tools 44 is transferred in the coupled state.

Figure 6:
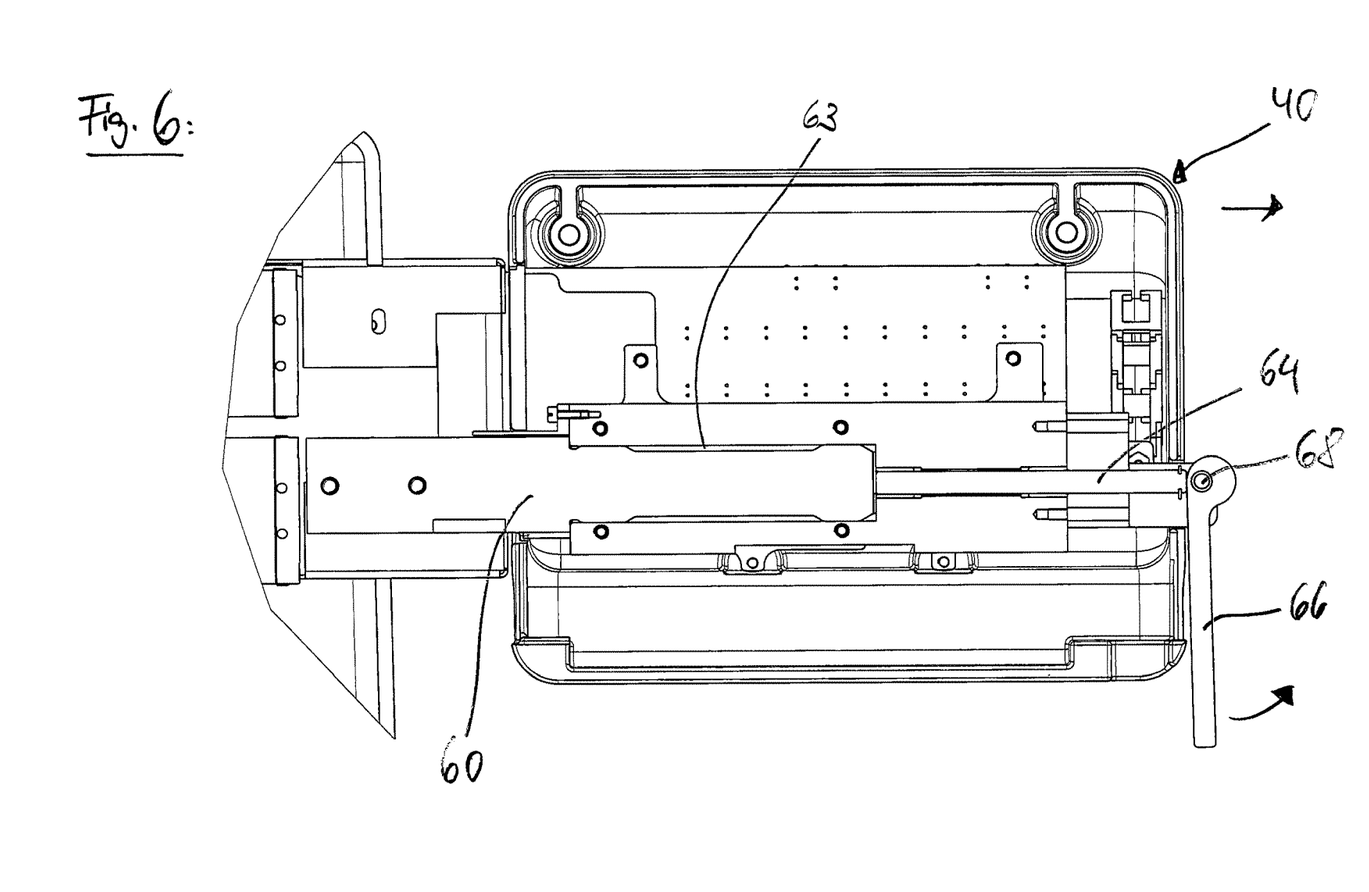
FIG. 6 shows a sectional view of the tool head of FIG. 5 in an enlarged scale.

The position of the stub axle 60 with respect to the tool head 40 in the coupled position can also be seen from FIG. 6, illustrating the tool head 40 of FIG. 5 in an enlarged sectional view. For better clarity, an illustration of the individual tools has been omitted in FIG. 6. It can be seen that the stub axle 60 couples with the recess 63 formed in the tool head 60 by positive and/or frictional engagement. For removal of the tool head, there is provided a release device comprising a first web 64 acting on stub axle 60, as well as a pivot lever 66 pivotally connected thereto. When lever 66 is pivoted in upward direction, as illustrated in FIG. 5 by an arrow, web 64 is shifted slightly towards stub axle 60 due to the somewhat eccentric arrangement of pivot joint 68. Due to the fact that pivot joint 68 is supported on tool head 40, the latter is displaced with respect to stub axle 60 in the direction of reduced engagement of the stub axle 60 in the recess in tool head 40, so that the tool head finally is disengaged completely from the stub axle and can be removed. A new tool head 40 can be simply slipped on then.

Figure 7A:
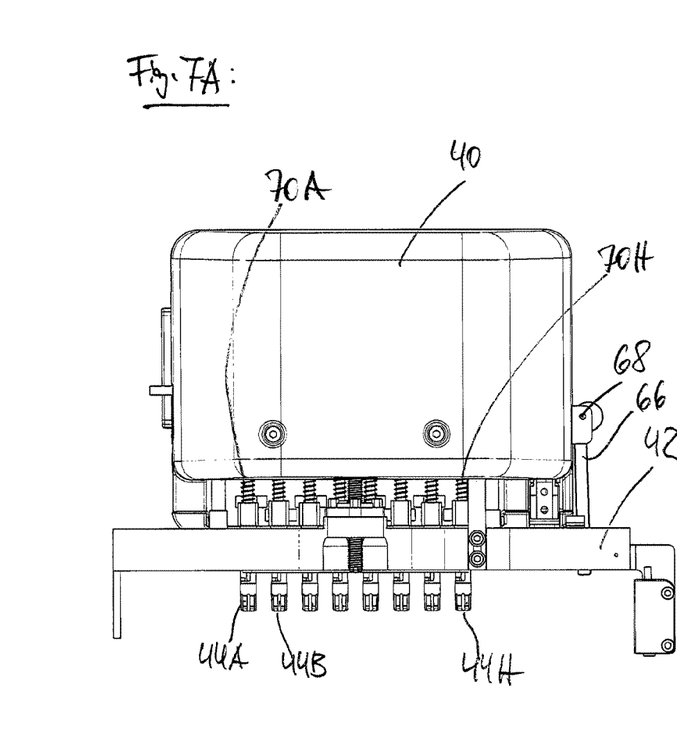
FIGS. 7A and 7B show a side view of the tool head of FIG. 5, each with a different number of tools for threadedly engaging and threadedly disengaging lids, respectively.
Figure 7B:
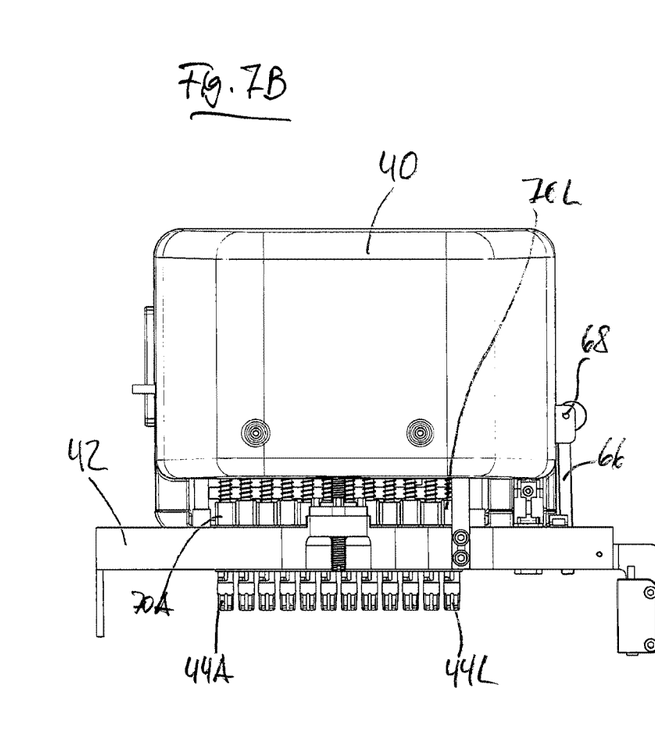

Finally, FIGS. 7A and 7B each illustrate a tool head 40 in a side view. Each of the tool heads 40 can easily be coupled to stub axle 60 and removed from the same, respectively, in accordance with the mechanism illustrated in FIG. 6. The tool head according to FIG. 7A is equipped with a total of 8 series-arranged manipulation tools 44A to 44H which are each suspended on tool carrier 42. Each of the tools 44A to 44H is supported to be rotatable about its central vertical axis and is rotatably driven via a respective rotary shaft 70A to 70H by means of a rotary drive accommodated in tool head 40. Tools 44A to 44H are adapted to threadedly disengage and threadedly engage lids having a screw cap from and with sample containers, respectively. The direction of rotation of tools 44A to 44H is preferably reversible, so that the tools can serve both for threadedly engaging and threadedly disengaging lids.

Differently from the tool head of FIG. 7A, the tool head illustrated in FIG. 7B is equipped with a total of 12 tools 44A to 44L which are also suspended on the tool carrier 42 in a row or series. Each of the tools 44A to 44L is coupled to a rotary drive accommodated in the tool head via a respective vertical rotary shaft 70A to 70L, as was also described with reference to FIG. 7A.

When processing otherwise similar sample containers which are to be processed in sample carriers in landscape arrangement and in sample carriers in portrait arrangement in alternating manner, the tool heads according to FIGS. 7A and 7B are accordingly attached to, and removed from, stub axle 60 in alternating manner. In the embodiment illustrated with 8 and 12 tools, respectively, this holds for sample carriers of SBS format with 96 sample containers in 8 rows with 12 sample containers each (landscape arrangement, processing by means of tool head 40 according to FIG. 7B) or in 12 rows with 8 sample containers each (portrait arrangement, processing by means of tool head 40 according to FIG. 7A).

The invention claimed is:

1. A sample manipulation device for removing lids from sample containers and placing lids onto sample containers, the sample manipulation device comprising:
   a sample unit; and
   a manipulation unit having at least one manipulation tool configured to remove and place a lid on a sample container, and configured to rotate to threadedly engage and threadedly disengage the lid from the sample container;
   wherein the sample unit and the manipulation unit are movable relative to each other along a movement direction;
   wherein the sample unit comprises a sample carrier receptacle configured to receive a sample carrier for holding one or more sample containers, said sample carrier extending in a longitudinal direction and a transverse direction orthogonal to said longitudinal direction, a dimension of the sample carrier being larger in the longitudinal direction than in the transverse direction;
   wherein the sample unit is transferable between a first orientation in which the longitudinal direction of the sample carrier received in the sample carrier receptacle is parallel to the movement direction between the sample unit and the manipulation unit, and a second orientation in which the transverse direction of the sample carrier received in the sample carrier receptacle is parallel to the movement direction between the sample unit and the manipulation unit;
   wherein the sample unit further comprises a sample carriage that is displaceable in the movement direction, and wherein the sample carrier receptacle is rotatably supported in the sample carriage; and
   wherein the sample carriage comprises a sample lid carrier receptacle in which a sample lid carrier associated with and having a configuration corresponding to the sample carrier can be received, the sample lid carrier configured to receive the lid removed from the sample container, wherein the sample lid carrier receptacle is formed such that, both in the first orientation of the sample unit and in the second orientation of the sample unit, the respectively associated sample lid carrier can be received in the same orientation in relation to the sample carrier received in the sample carrier receptacle.

2. The sample manipulation device according to claim 1, wherein the sample carrier has a first axis of symmetry extending in the longitudinal direction and a second axis of symmetry extending in the transverse direction and orthogonal to the first axis of symmetry.

3. The sample manipulation device according to claim 1, wherein, for transfer between the first orientation and the second orientation, the sample carrier receptacle is rotatable about an axis of rotation orthogonal to a plane defined by the longitudinal direction and the transverse direction.

4. The sample manipulation device according to claim 3, wherein the axis of rotation is a vertical axis and arranged centrally with respect to the sample carrier received in the sample carrier receptacle.

5. The sample manipulation device according to claim 1, further comprising a rotary drive acting on the sample carrier received in the sample carrier receptacle for rotation thereof at least between said first and second orientations.

6. The sample manipulation device according to claim 5, wherein the sample carrier receptacle is coupled with a sample table that is rotatable about a vertical axis, wherein the sample carrier receptacle is formed in the sample table.

7. The sample manipulation device according to claim 6, wherein the sample table is acted upon by the rotary drive, wherein the sample table has at least one circular peripheral surface for cooperation with the rotary drive.

8. The sample manipulation device according to claim 7, wherein the at least one circular peripheral surface of the sample table is formed with teeth cooperating with an output pinion of the rotary drive, or has a driving surface frictionally cooperating with an output wheel of the rotary drive.

9. The sample manipulation device according to claim 1, wherein the sample lid carrier receptacle in a plan view has an outline resulting from a combination of outlines of two sample carrier receptacles rotated relative to each other by an angle of 90 degrees about a common axis of rotation, wherein the sample lid carrier receptacle has a cross-shaped outline in a plan view.

10. The sample manipulation device according to claim 1, further comprising a linear drive acting on the sample unit and adapted to displace the sample unit in the movement direction in relation to the manipulation unit.

11. The sample manipulation device according to claim 10, wherein the linear drive is arranged underneath the sample unit and engages the sample carriage.

12. The sample manipulation device according to claim 1, wherein the at least one manipulation tool is attached to the manipulation unit so as to be rotatable about a vertical axis, and is displaceable in a vertical direction in order to move the at least one manipulation tool towards the sample unit.

13. The sample manipulation device according to claim 12, wherein the manipulation unit comprises a plurality of manipulation tools that are lined up in a direction orthogonal to a vertical plane defined by the movement direction of the manipulation unit.

14. The sample manipulation device according to claim 1, wherein the manipulation unit comprises an exchangeably mounted tool head, the tool head as a unit being displaceable in a vertical direction and the at least one manipulation tool being attached to the tool head so as to be rotatable about a vertical axis.

15. The sample manipulation device according to claim 1, further comprising a sample container identification device for identification of the sample carrier and an individual sample container located in the sample carrier.

16. The sample manipulation device according to claim 15, wherein the sample container identification device is formed such that it is capable of recognizing identification patterns located at the bottom of a respective sample container.

17. The sample manipulation device according to claim 15, wherein the sample container identification device comprises at least one optical sensor.

18. The sample manipulation device according to claim 1, wherein the manipulation unit has a plurality of manipulation tools, each configured to remove and place a lid on a respective sample container.

* * * * *